United States Patent [19]
Lewis

[11] Patent Number: 6,044,845
[45] Date of Patent: Apr. 4, 2000

[54] METHODS AND SYSTEMS FOR TREATING ISCHEMIA

[75] Inventor: Brian Douglas Lewis, Stanford, Calif.

[73] Assignee: Salient Interventional Systems, Inc., Stanford, Calif.

[21] Appl. No.: 09/018,214

[22] Filed: Feb. 3, 1998

[51] Int. Cl.[7] .................................................. A61B 19/00
[52] U.S. Cl. .................................. 128/898; 604/4; 604/7; 604/8; 604/48; 604/49
[58] Field of Search ......................... 128/898; 604/4, 604/7, 8, 48, 49–53, 96, 102

[56] References Cited

U.S. PATENT DOCUMENTS

| | | | |
|---|---|---|---|
| 4,468,216 | 8/1984 | Muto | 604/43 |
| 4,564,014 | 1/1986 | Fogarty et al. | . |
| 4,661,094 | 4/1987 | Simpson | 604/53 |
| 4,666,426 | 5/1987 | Aigner | 604/5 |
| 4,804,358 | 2/1989 | Karcher et al. | 600/17 |
| 4,850,969 | 7/1989 | Jackson | 604/96 |
| 4,921,483 | 5/1990 | Wijay et al. | 604/96 |
| 5,066,282 | 11/1991 | Wijay et al. | 604/152 |
| 5,090,960 | 2/1992 | Don Michael | 604/101 |
| 5,106,363 | 4/1992 | Nobuyoshi | 604/4 |
| 5,149,321 | 9/1992 | Klatz et al. | 604/52 |
| 5,158,540 | 10/1992 | Wijay et al. | 604/43 |
| 5,184,627 | 2/1993 | de Toledo | 128/772 |
| 5,186,713 | 2/1993 | Raible | 604/4 |
| 5,403,274 | 4/1995 | Cannon | 604/9 |
| 5,407,424 | 4/1995 | LaFontaine et al. | 604/4 |
| 5,425,723 | 6/1995 | Wang | 604/280 |
| 5,451,207 | 9/1995 | Yock | 604/53 |
| 5,462,523 | 10/1995 | Samson et al. | 604/30 |
| 5,505,710 | 4/1996 | Dorsey, III | . |
| 5,531,715 | 7/1996 | Engelson et al. | 604/265 |
| 5,584,804 | 12/1996 | Klatz et al. | 604/24 |
| 5,624,396 | 4/1997 | McNamara et al. | . |
| 5,626,564 | 5/1997 | Zhan et al. | . |
| 5,643,228 | 7/1997 | Schucart et al. | 604/264 |
| 5,782,797 | 7/1998 | Schweich, Jr. et al. | . |

FOREIGN PATENT DOCUMENTS

| | | | |
|---|---|---|---|
| 1322315 | 9/1993 | Canada | A61M 17/02 |
| 0476796 | 3/1992 | European Pat. Off. | . |
| 3731590 | 7/1988 | Germany | . |
| WO 92/20398 | 11/1992 | WIPO | A61M 29/00 |
| WO 97/19713 | 6/1997 | WIPO | . |

*Primary Examiner*—Mickey Yu
*Assistant Examiner*—Dinh X. Nguyen
*Attorney, Agent, or Firm*—Townsend and Townsend and Crew LLP

[57] ABSTRACT

Methods for treating total and partial occlusions employ a perfusion conduit which is penetrated through the occlusive material. Oxygenated blood or other medium is then perfused through the conduit to maintain oxygenation and relieve ischemia in tissue distal to the occlusion. Optionally, the occlusion may be treated while perfusion is maintained, typically by introducing a thrombolytic or other agent into the occlusive material using the perfusion conduit. Such methods are particularly suitable for treating acute stroke to prevent irreversible damage to the cerebral tissue.

53 Claims, 7 Drawing Sheets

METHODS AND SYSTEMS FOR TREATING ISCHEMIA

BACKGROUND OF THE INVENTION

1. Field of the Invention

The present invention relates generally to medical devices and methods. More particularly, the present invention relates to catheters, systems, kits, and methods for treating ischemia, such as intracerebral ischemia associated with stroke.

Hemodynamically significant restriction of arterial blood flow can lead to oxygen deprivation in tissue, referred to as ischemia, and can quickly lead to cell death and organ dysfunction. The brain is the organ most sensitive to ischemia, followed by the heart, the abdominal organs, and the extremities. The brain will usually not tolerate ischemia for very long without massive neuron death (stroke). When treating ischemic events in the brain, it is imperative to restore blood flow quickly and safely.

The most common causes of acute arterial ischemia in the cerebrovasculature are thrombosis and embolus. Thrombus usually forms at the site of a pre-existing atherosclerotic lesion and can cause an acute occlusion. Atherosclerosis can occur at any location within the arteries that deliver blood from the heart to the brain, but the most common locations of significant atherosclerosis are the cervical carotid artery at the carotid bifurcation, the proximal middle cerebral artery, and the vertebrobasilar arterial system. Clinically significant atherosclerosis also can occur in other intracerebral vessels.

Emboli are formed when previously stable thrombus or atheroma is released into the blood stream and becomes lodged in smaller blood vessels. Emboli can originate from atherosclerotic lesions and from within the cardiac chambers. They can cause acute obstructions of blood vessels, resulting in tissue hypoxia and neuron death. Further obstruction can also occur distally to the embolus due to secondary inflammatory responses and other reactions. Transient ischemic attacks (TIA's) occur with temporary and intermittent obstructions, allowing for neuron recovery. Stroke occurs with longer term obstruction to blood flow.

Traditional therapy of acute stroke has been limited to the delivery of supportive measures. Newer treatments for stroke attempt to relieve or bypass vessel occlusion before neuron death occurs. In the life threatening emergency of acute stroke, there is a time-limited window of opportunity for treatment after the onset of symptoms. After this treatment window has closed, there is minimal opportunity for recovery of neuronal function. Furthermore, restoring blood perfusion late in the therapeutic window can cause cerebral hemorrhage or edema and progression of symptoms, referred to as the "reperfusion syndrome." For this reason, recent emphasis has been placed on the early treatment of patients, usually within six hours of the onset of symptoms, and on relieving the obstruction emergently.

A number of techniques have been proposed which employ site-specific administration of thrombolytic drugs and/or mechanical means, laser or ultrasound energy sources to remove thrombus. Angioplasty, atherectomy and stent placement are employed to relieve atherosclerotic stenoses. These methods all require positioning catheter based devices at or near the site of the arterial obstruction. The primary objective is to restore blood flow as quickly as possible. Such devices, however, require significant time to position and use. There are also risks of damaging the obstructed artery, of dislodging and embolizing blood thrombus or atherosclerotic plaque, of inducing intracerebral hemorrhage or other serious complications. Directed thrombolysis using currently available catheters and guidewires often takes many hours to complete. While excellent technical results are feasible, many patients cannot tolerate the wait and their condition can deteriorate during the procedure. Surgical bypass does not work as well as standard medical therapy in preventing stroke recurrence and is only rarely performed.

New classes of "neuroprotectant" agents and "angiogenesis promoters" have been proposed. These drugs may extend the effective therapeutic window for stroke therapy and permit better long term outcomes. Their use, however, may require novel delivery systems and often require that the patient be stabilized and ischemia relieved in order to obtain a lasting clinical improvement.

For these reasons, it would be desirable to provide improved methods and apparatus for treating acute ischemic conditions, particularly stroke. It would be further desirable if such methods and apparatus were also useful for treating chronic ischemia in other portions of a patient's vasculature, including the coronary vasculature and the peripheral and mesenteric vasculature. The methods and apparatus should be capable of rapidly reestablishing blood flow at a rate sufficient to relieve ischemia distal to the occlusion, and would ideally (but not necessarily) be adaptable for use both in an emergency situation (i.e., outside the hospital) as well as within a hospital environment. The methods and apparatus should provide for control over the rate of blood flow and/or cessation of blood flow to the ischemic region in order to avoid reperfusion injury. In addition to relieving ischemia, the methods and devices of the present invention will preferably further provide access and support for performing other therapeutic interventions to treat the occlusion, including both drug interventions and mechanical interventions. Additionally, the methods and devices should be adaptable to use access routes of a type which are familiar to interventionalists so as to permit rapid and wide spread adoption. At least some of these objectives will be met by different aspects of the present invention.

2. Description of the Background Art

U.S. Pat. No. 5,149,321 describes an emergency system for infusing an oxygenated medium into the cerebral vasculature in patients following a heart attack. Active perfusion through coronary angioplasty catheters is described in a number of patents and published applications, including U.S. Pat. Nos. 5,106,363; 5,158,540; 5,186,713; and 5,407,424; Canadian Patent 1,322,315; and WO 97/19713. The latter describes perfusion of an oxygenated medium through a guidewire. Perfusion and/or infusion catheters and systems are described in a number of patents, including U.S. Pat. Nos. 5,584,804; 5,090,960; 4,611,094; 4,666,426; 4,921,483; 5,643,228; 5,451,207; 5,425,723; 5,462,523; 5,531,715; 5,403,274; 5,184,627; 5,066,282; 4,850,969; 4,804,358; 4,468,216; and WO 92/20398. U.S. Pat. No. 5,090,960 describes a passive perfusion catheter having spaced-apart balloons and a suction tube for recirculating a thrombolytic agent.

SUMMARY OF THE INVENTION

The present invention provides methods, apparatus, and kits for treating patients suffering from ischemia resulting from the partial or total obstruction of a blood vessel. Usually, the obstructions will be high-grade blockages, e.g., those which result in greater than 75% flow reduction, but in some instances they may be of a lower grade, e.g., ulcerated lesions. As used hereinafter, the terms "obstruction," "occlusion," and "blockage" will be used generally interchangeably and will refer to both total obstructions where substantially all flow through a blood vessel is stopped as well as to partial obstructions where flow through the blood vessel remains, although at a lower rate than if the obstruction were absent.

Preferred use of the present invention is for the treatment of patients suffering from acute stroke resulting from a sudden, catastrophic blockage of a cerebral artery. The present invention, however, will also be useful for treating acute blockages in other portions of the vasculature as well as for treating chronic occlusions in the cerebral, cardiac, peripheral, mesenteric, and other vasculature. Optionally, the methods of the present invention may be used to facilitate dissolving or removing the primary obstruction responsible for the ischemia, e.g., by drug delivery, mechanical intervention, or the like, while perfusion is maintained to relieve the ischemia.

Methods according to the present invention comprise penetrating a perfusion conduit through the blockage and subsequently pumping an oxygenated medium through the conduit at a rate or pressure sufficient to relieve ischemia downstream from the blockage. Usually, the oxygenated medium is blood, more usually being blood obtained from the patient being treated. In some instances, however, it will be possible to use other oxygenated media, such as perfluorocarbons or other synthetic blood substitutes. In a preferred aspect of the present invention, the pumping step comprises drawing oxygenated blood from the patient, and pumping the blood back through the conduit at a controlled pressure and/or rate, typically a pressure within the range from 50 mmHg to 300 mmHg, preferably at a mean arterial pressure in the range from 50 mmHg to 150 mmHg, and at a rate in the range from 30 cc/min to 360 cc/min, usually from 30 cc/min to 240 cc/min, and preferably from 30 cc/min to 180 cc/min, for the cerebral vasculature. Usually, pressure and flow rate will both be monitored. Pressure is preferably monitored using one or more pressure sensing element(s) on the catheter which may be disposed distal and/or proximal to the obstruction where the blood or other oxygenated medium is being released. Flow rate is easily monitored on the pumping unit in a conventional manner. Conveniently, the blood may be withdrawn through a sheath which is used for percutaneously introducing the perfusion conduit.

It will usually be desirable to control the pressure and/or flow rate of the oxygenated medium being delivered distally to the occlusion. Usually, the delivered pressure of the oxygenated medium should be maintained below the local peak systolic pressure and/or mean arterial blood pressure of the vasculature at a location proximal to the occlusion. It will generally be undesirable to expose the vasculature distal to the occlusion to a pressure above that to which it has been exposed prior to the occlusion. Pressure control of the delivered oxygenated medium will, of course, depend on the manner in which the medium is being delivered. In instances where the oxygenated medium is blood which is being passively perfused past the occlusion, the delivered pressure will be limited to well below the inlet pressure, which is typically the local pressure in the artery immediately proximal to the occlusion. Pressure control may be necessary, however, when the oxygenated medium or blood is being actively pumped. In such cases, the pump may have a generally continuous (non-pulsatile) output or in some cases may have a pulsatile output, e.g., being pulsed to mimic coronary output. In the case of a continuous pump output, it is preferred that the pressure being released distally of the occlusion be maintained below the mean arterial pressure immediately distal to the occlusion, usually being below 150 mmHg, often being below 100 mmHg. In the case of a pulsatile pump output, the peak pressure should be maintained below the peak systolic pressure upstream of the occlusion, typically being below 200 mmHg, usually being below 150 mmHg. Control may be based on the measured pressure proximal of the occlusion or could be based on an average value of the mean arterial pressure or peak systolic pressure expected for most patients.

In some instances, it will be desirable to initiate the flow of blood or other oxygenated medium slowly and allow the flow rate and pressure to achieve their target values over time. For example, when actively pumping the oxygenated medium, the pumping rate can be initiated at a very low level, typically less than 30 cc/min, often less than 10 cc/min, and sometimes beginning at essentially no flow and can then be increased in a linear or non-linear manner until reaching the target value. Rates of increase can be from 1 cc/min/min to 360 cc/min/min, usually being from 5 cc/min/min to 100 cc/min/min.

While pumping will usually be required to maintain adequate perfusion, in some instances passive perfusion may be sufficient. In particular, perfusion of the smaller arteries within the cerebral vasculature can sometimes be provided using a perfusion conduit having inlet ports or apertures on a proximal portion of the conduit and outlet ports or apertures on a distal portion of the conduit. By then positioning the inlet and outlet ports on the proximal and distal sides of the obstruction, respectively, the natural pressure differential in the vasculature will be sufficient to perfuse blood through the conduit lumen past the obstruction. Usually, the inlet ports on the perfusion conduit will be located at a location as close to the proximal side of the occlusion as possible in order to minimize the length of perfusion lumen through which the blood will have to flow. In some instances, however, it may be necessary to position the inlet ports sufficiently proximal to the occlusion so that they lie in a relatively patent arterial lumen to supply the necessary blood flow and pressure. The cross-sectional area of the perfusion lumen will be maintained as large as possible from the point of the inlet ports to the outlet ports. In this way, flow resistance is minimized and flow rate maximized to take full advantage of the natural pressure differential which exists.

While perfusion is maintained through the perfusion conduit, treatment of the blood vessel blockage may be effected in a variety of ways. For example, thrombolytic, anticoagulant and/or anti-restenotic agents, such as tissue plasminogen activator (tPA), streptokinase, urokinase, heparin, or the like, may be administered to the patient locally (usually through the perfusion catheter) or systemically. In a preferred aspect of the present invention, such thrombolytic and/or anticoagulant agents may be administered locally to the arterial blockage, preferably through a lumen in the perfusion catheter itself. Such local administration can be directly into the thrombus, e.g., through side infusion ports which are positioned within the thrombus while the perfusion port(s) are positioned distal to the thrombus. Optionally, a portion of the blood which is being perfused could be added back to or otherwise combined with thrombolytic and/or anticoagulant agent(s) being administered through the catheter. The addition of blood to certain thrombolytic agents will act to catalyze the desired thrombolytic activity. The availability of the patient blood being perfused greatly facilitates such addition. It would also be possible to deliver the agent(s) through the same lumen and distal port(s) as the blood being pumped back through the perfusion lumen so that the agents are delivered distally of the catheter. The latter situation may be used advantageously with neuroprotective agents, vasodilators, antispasmotic drugs, angiogenesis promoters, as well as thrombolytics, anticoagulants, and anti-restenotic agents, and the like. The two approaches, of course, may be combined so that one or more agents, such as thrombolytic agents, are delivered directly into the thrombus while neuroprotective or other agents are delivered distally to the thrombus. Moreover, such delivery routes can also be employed simultaneously with systemic delivery of drugs or other agents to the patient.

Alternatively or additionally, mechanical interventions may be performed while the vasculature is being perfused according to the present invention. For example, a perfusion conduit may have a very low profile and be used as a guide element to introduce an interventional catheter, such as an angioplasty catheter, an atherectomy catheter, a stent-placement catheter, or the like.

The perfusion of the oxygenated medium may be performed for a relatively short time in order to relieve ischemia while other interventional steps are being taken, or may be performed for a much longer time either in anticipation of other interventional steps and/or while other long-term interventions are being performed. In particular, when thrombolytic and/or anticoagulant agents are being used to treat the primary blockage, the perfusion can be continued until the blockage is substantially relieved, typically for at least thirty minutes, often for four to eight hours, or longer. In other instances, perfusion can be maintained for much longer periods, e.g., more than one week, more than two weeks, more than a month, or even longer.

In addition to delivering oxygen to the ischemic region distal to the primary occlusion, the blood or other oxygenated medium may carry other treatment agents, including thrombolytic agents, anticoagulant agents, tissue preservative agents, and the like. Moreover, in order to further preserve the cerebral tissue distal to the blockage, the oxygenated medium may be cooled to below body temperature, e.g., to a temperature in the range from 2° C. to 36° C., typically from 25° C. to 36° C., in order to cool and preserve the tissue. Cooling may be effected externally as part of the extracorporeal pumping system and/or may be effected using a thermoelectric or Joule-Thomson expansion cooler on the catheter itself.

Patients suffering from ischemia resulting from acute or chronic occlusion in the cerebral vasculature may be treated according to a preferred method. A perfusion conduit is introduced to the patient's vasculature, and a distal port on the conduit is guided through the occlusion in the cerebral vasculature. Blood, optionally oxygenated and/or superoxygenated, is obtained from the patient and perfused back to the patient through the distal port on the conduit past the occlusion at a rate sufficient to relieve the ischemia. The oxygenated blood may be arterial blood which may be returned to the patient without further oxygenation. Alternatively, arterial or venous blood can be oxygenated in suitable apparatus external to the patient and returned to the patient. External oxygenation allows the blood to be "superoxygenated," i.e., oxygenated at higher levels than would normally be available from arterial blood. Usually, the method further comprises delivering a therapeutic agent to the patient while the perfusing step is continued, usually being a thrombolytic agent which is delivered through the conduit directly to the vascular occlusion. The occlusion is usually in either a carotid artery, vertebral artery, proximal subclavian artery, brachiocephalic artery, or an intracerebral artery, and the conduit is usually introduced via the femoral artery in a conventional intravascular approach, typically being positioned over a guidewire which is first used to cross the occlusion. Alternatively, the conduit may be introduced through the axillary or brachial arteries, also in a conventional manner.

Apparatus according to the present invention comprises perfusion/infusion catheters which include a catheter body having a proximal end and a distal end. The catheter body has at least two lumens, which may be formed as part of a single extrusion or which may be formed as separate tubes. When formed as separate tubes, the tubes may be fixed relative to each other or may be provided with appropriate sliding seals to permit them to slide relative to each other. Additional lumens and/or tubes may also be provided for purposes discussed in more detail below. Often, although not always, the catheters will be free from external dilatation balloons or other external structure which could complicate penetration of the distal end of the catheter through an obstruction.

A first embodiment of the catheter is characterized by a large diameter proximal section and a small diameter distal section, where at least two isolated lumens extend from the proximal end of the catheter body through both sections to near the distal end of the catheter body. One of the lumens will extend entirely through the catheter body and usually have side ports over a distal length thereof. The other lumen will usually terminate some distance proximal of the distal tip of the catheter body and will also usually have side ports over a distal length thereof. The proximal section has an outer diameter in the range from 1 mm to 3 mm, usually from 1.5 mm to 2.5 mm, and typically from 1.5 mm to 2 mm, and the distal section has an outer diameter in the range from 0.5 mm to 2 mm, preferably from 0.5 mm to 1.5 mm. The first isolated lumen which extends entirely through the catheter body will usually be tapered, i.e., have a larger diameter over a proximal length thereof than over a distal length thereof. Usually, the first isolated lumen will have an inner diameter in the range from 0.75 mm to 1.25 mm in the proximal section, more usually being from 0.9 mm to 1.1 mm in the proximal section, and an inner diameter in the range from 0.25 mm to 1 mm in the distal section, usually being from 0.3 mm to 0.75 mm in the distal section. The second isolated lumen will usually be disposed annularly about the first isolated lumen and will have an inner diameter in the range from 0.9 mm to 2.9 mm in the proximal section, usually from 1.4 mm to 1.9 mm in the proximal section, and an inner diameter in the range from 0.4 mm to 1.9 mm in the distal section, usually in the range from 0.5 mm to 1.5 mm in the distal section. The second, outer annular lumen will typically terminate from 5 cm to 25 cm from the distal end of the catheter body.

Apparatus according to the present invention further comprises systems including a perfusion/infusion catheter as set forth above in combination with a sheath for percutaneously introducing the perfusion/infusion catheter and a pump for receiving blood from the sheath and delivering blood back to the catheter. Optionally, an infusion device may be provided in the system for infusing a drug to a lumen of the perfusion/infusion catheter.

The present invention still further comprises kits, including a perfusion catheter and instructions for use setting forth a method for penetrating the catheter through a blockage in a patient's vasculature and thereafter perfusing an oxygenated medium through the conduit to relieve ischemia. Kits will usually further comprise a container, such as a pouch, tray, box, tube, or the like, which contains the catheter as well as the instructions for use. Optionally, the instructions for use set forth on a separate instructional sheet within the package, but alternatively could be printed in whole or in part on the packaging itself. Optionally, other system components useful for performing the methods of the present invention could be provided within the kit, including guidewires, introductory sheaths, guiding catheters, and the like.

DESCRIPTION OF THE SPECIFIC EMBODIMENTS

Figure 1A:
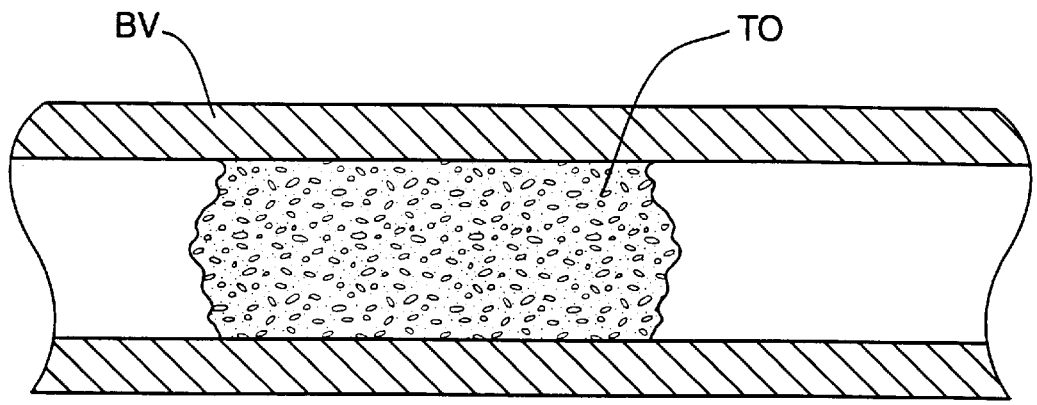
FIGS. 1A–1C illustrate an exemplary protocol for treating a total occlusion in a blood vessel according to the method of the present invention.

The general principles of the present invention for treating partial and total occlusions within a patient's vasculature will be described in connection with FIGS. 1A–1C. A blood vessel BV which is usually an artery, more usually a cerebral artery, such as a carotid artery, vertebral artery, or an intracerebral artery, is obstructed by a total occlusion TO. The occlusion may result from thrombosis at a pre-existing atherosclerotic lesion or may result from the shedding of an embolus from an artery which flows distally to the particular vessel in which the occlusion occurs. Usually, the occlusion will occur abruptly and the sudden loss of perfusion through the blood vessel distal to the total occlusion TO will place the patient at great risk of neuron death. As discussed above in the Background section, it is usually necessary to reestablish perfusion within a matter of hours in order to avoid significant tissue damage or death, particularly in the case of strokes. While six hours is often considered a maximum delay, earlier treatment is much more desirable.

The present invention provides a method for very quickly reestablishing perfusion through the total occlusion TO. Such perfusion is established using a perfusion conduit 10 (FIG. 1C) through which oxygenated blood or an oxygenated synthetic medium, such as a perfluorocarbon oxygen carrier, is actively pumped back through a lumen of the catheter from a source 12. Usually, the conduit will include side perfusion ports 14 near its distal end 16 in order to enhance perfusion and reduce hemolysis (when blood is the oxygenated medium). Optionally, proximal portions of the conduit 10 (not shown) may have enlarged lumen diameters in order to reduce flow resistance and shear forces to further reduce or prevent hemolysis. It will be appreciated that while the distal portion of the conduit 10 will usually have a relatively low profile to access small diameter blood vessels, the proximal portions can be made significantly larger to improve the hemodynamic flow and handling characteristics and reduce hemolysis.

Figure 1B:
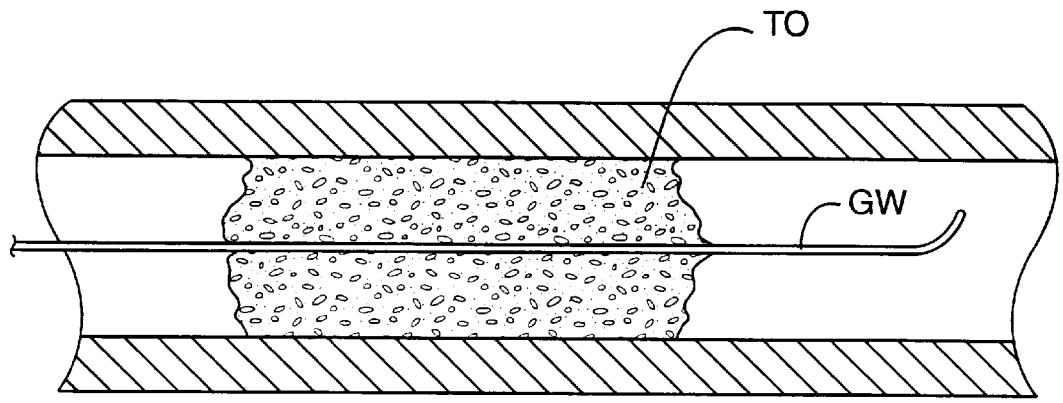
Figure 1C:
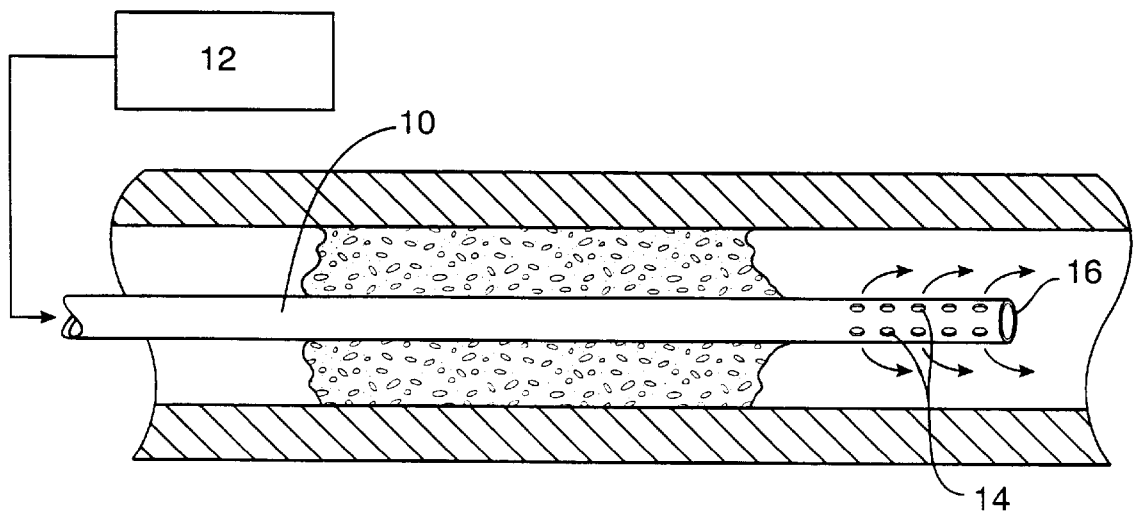

Optionally, the conduit 10 will be introduced over a conventional guidewire GW which is initially used to cross the total occlusion TO, as shown in FIG. 1B. In other instances, however, the perfusion conduit 10 may be adapted so that it is able to cross the total occlusion TO without the use of a conventional guidewire. In some cases, the perfusion conduit may be in the form of a guidewire, e.g., a tapered guidewire, which is suitable for both guiding through the vasculature to the site of the total or partial occlusion as well as crossing the occlusion.

The perfusion conduit 10 may be introduced from any normal intravascular introduction site, e.g., through the femoral artery using the Seldinger technique. Alternatively, the infusion conduit can be introduced through the axillary and other arteries.

A system 20 suitable for treating occlusions within the cerebral vasculature is illustrated in FIGS. 2–6. The system 20 includes a perfusion conduit in the form of intravascular catheter 22. The catheter 22 comprises a catheter body 24 having a distal end 26 and a proximal end 28. The catheter body 24 comprises a pair of coaxial tubular elements, including an outer tube 30 and an inner tube 32. Proximal hub 34 comprises a first port 36 which is fluidly coupled to an interior lumen of the inner tube 32 and a second port 38 which is fluidly coupled to an annular lumen between the exterior surface of inner tube 32 and the interior of tube 30. Proximal port 40 (typically a hemostasis valve) also communicates with the lumen of the inner tube 32 and is suitable for intravascular positioning of the catheter 22 over a guidewire.

The system usually further includes a guiding catheter 50 having dimensions and characteristics suitable for introducing the catheter 22 to the desired intravascular target site. Although illustrated as having a straight configuration, the guiding catheter 50 will often have a preformed, curved tip selected specifically to reach the intravascular target site, and the guiding catheter could further be reinforced (e.g., braided), have a variable stiffness over its length, have a variable diameter, or the like. The system 20 will usually still further comprise a sheath 60 which is used to percutaneously access the vasculature at the introductory site, e.g., in the femoral artery. The sheath 60 has a proximal hub 61 including at least one side arm 62. The hub 61 receives the catheter 22 therethrough and will include a mechanism for maintaining hemostasis about the catheter. The side arm 62 permits withdrawal of blood for oxygenation and return to the patient according to the present invention. Other side arm(s) may be provided for removal of blood (optionally combined with drugs being delivered back to the patient), for infusing agents through the sheath 60, or for other purposes. Entry of blood into the lumen of the sheath is optionally facilitated by side ports 64 formed over at least a distal portion of the sheath.

The catheter body 24 is tapered in the distal direction, i.e., the diameter is larger near the proximal end 28 than at the distal end 26. As illustrated in FIGS. 2–6, the outer tube 30 has a large diameter proximal section (observed in FIG. 3) and a smaller diameter distal section (observed in FIGS. 4 and 5). Similarly, the inner tube 32 has a large diameter proximal section (shown in FIG. 3) and a smaller diameter distal section (shown in FIGS. 4–6). The particular outer diameters and inner lumen diameters of both the outer tube 30 and inner tube 32 are within the ranges set forth above. Since the distal terminii of the outer tube 30 and inner tube 32 are staggered, the catheter body 24 is tapered in three stages, with a first diameter reduction occurring at location 33 (FIG. 2) where the diameter of the outer tubular member 30 is reduced from the diameter shown in FIG. 3 to the diameter shown in FIG. 4. The second diameter reduction occurs at location 35 where the outer tubular member 30 terminates, leaving the outer surface of the inner tubular member 32 to define the catheter body.

Figure 3:
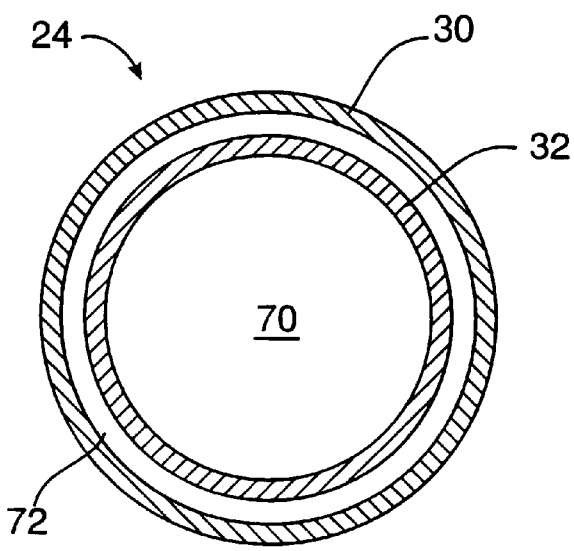
FIG. 3 is a cross-sectional view taken along line 3—3 of FIG. 2.
Figure 4:
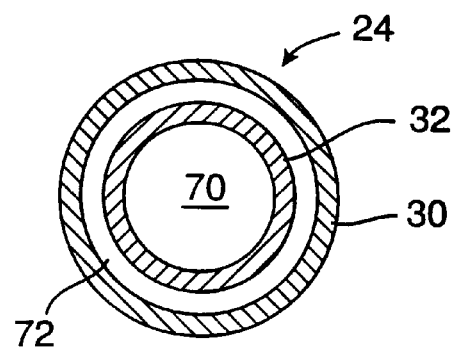
FIG. 4 is a cross-sectional view taken along line 4—4 of FIG. 2.

Such tapered configurations are preferred since they maximize the cross-sectional area of the flow lumens over the length of the catheter to reduce flow resistance for both the blood (or other oxygenated medium) and the drug to be delivered. As can be seen in FIG. 3, lumen 70 of the inner tubular member 32 which carries the blood is maximized until the diameter is reduced near the distal end of the catheter, as shown in FIG. 4. Similarly, the annular lumen 72 which carries the drug is maximized over the proximal portion before it is reduced after the transition at location 33. Maintaining the larger diameters and lumen areas is desirable in order to decrease flow resistance and shear forces to reduce or eliminate hemolysis as the blood is introduced through the entire catheter length. Similarly, a reduction in flow resistance to the drug being introduced facilitates drug delivery during the procedure.

Figure 2:
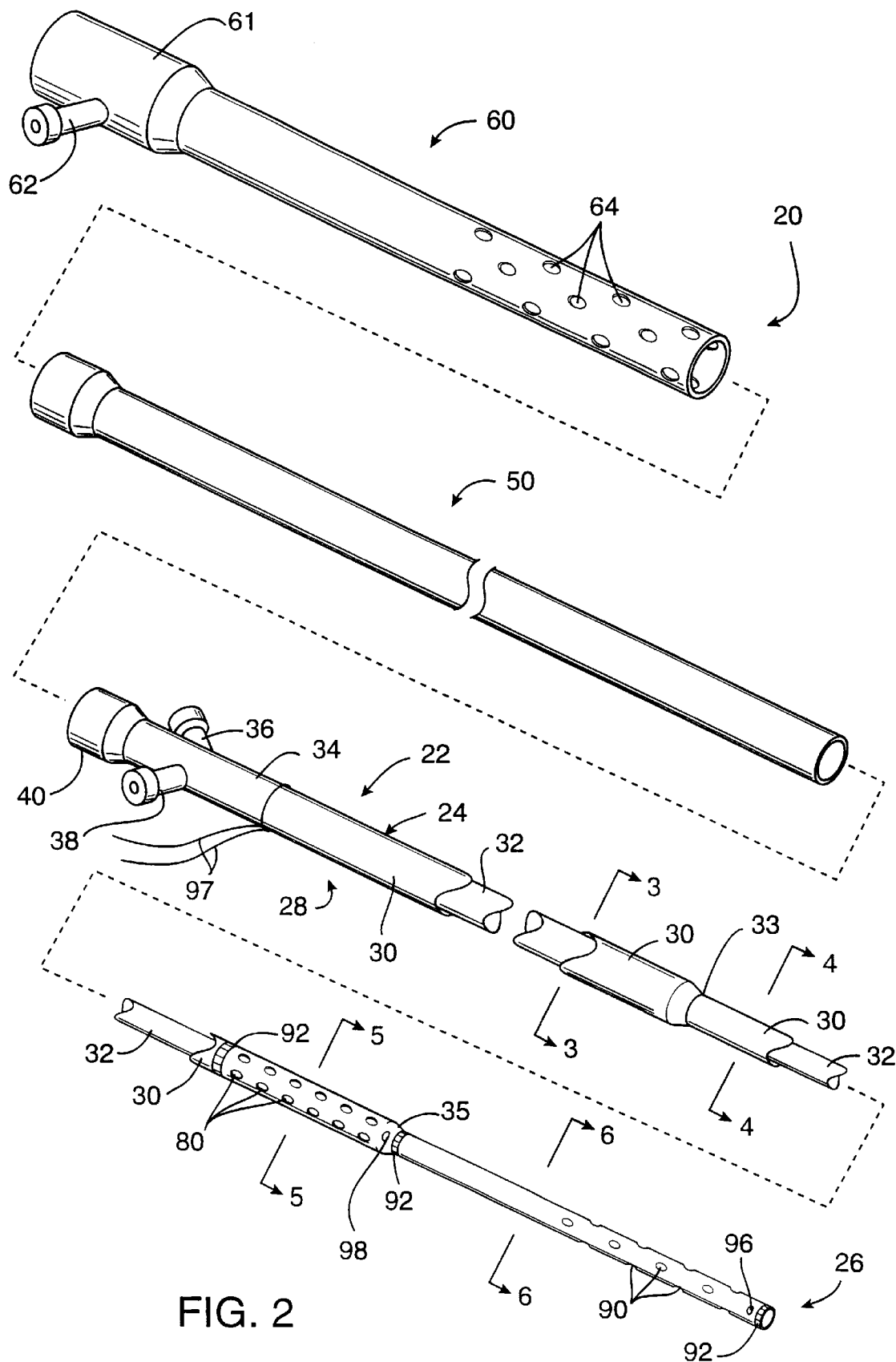
FIG. 2 illustrates an exemplary system for treating a total occlusion within a patient's cerebral vasculature according to the present invention.
Figure 5:
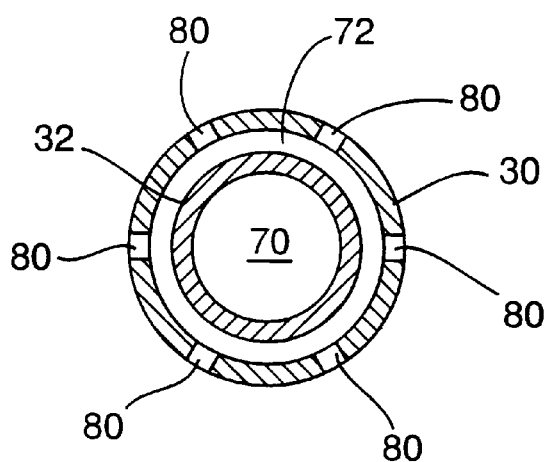
FIG. 5 is a cross-sectional view taken along line 5—5 of FIG. 2.
Figure 6:
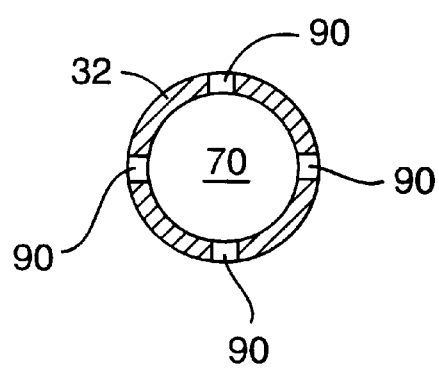
FIG. 6 is a cross-sectional view taken along line 6—6 of FIG. 2.

Side wall penetrations 80 are provided in a distal portion 26 of the outer tubular member 30, as best seen in FIGS. 2 and 5. The penetrations 80 will be useful for delivering a therapeutic agent through port 38 in order to treat the primary occlusion, as described in more detail hereinafter.

Similarly, ports 90 may be formed over at least a distal portion of the inner tubular member 32 which extends beyond the distal end of the outer tubular member 30. The penetrations 90 will be available to release blood or other oxygenated medium that is being perfused back to the patient through port 36 and the continuous lumen of the tube 32. Note that while the lumen 70 of tube 32 will be available for introduction of the catheter 22 over a guidewire, the guidewire may be at least partially withdrawn from the lumen 70 in order to further decrease blood flow resistance as it is perfused back to the patient.

Optionally, the catheter 22 may comprise at least one pressure sensing element 96 disposed at a location near where the blood or other oxygenated medium is returned to the blood vessel. Preferably, the pressure sensing element 96 may be a piezoelectric or other solid state pressure sensing device and will be connected through the hub 34 by a pair of wires 97 which may be connected to conventional electronic devices for measuring pressure. Thus, pressure may be measured and used for controlling rate and/or pressure of blood or other oxygenated medium pumped back to the patient using conventional analog or digital control circuitry. A pressure control point will be selected, usually within the ranges set forth above, and the rate or pressure of oxygenated medium being pumped back through the catheter 22 will be controlled to maintain the control point. Conventional control algorithms, such as proportional, derivative, integral, and combinations thereof, may be employed for maintaining the desired control point.

In some instances, it will be desirable to provide at least a second pressure sensing element 98 which will be located proximal to the obstruction when the catheter is in use. For example, the pressure sensing element 98 may be near the location 35 where the outer tubular member 30 terminates. The sensor 98 will permit monitoring of the pressure in the vasculature proximal of the occlusion, which pressure will usually approximate that of the vasculature in the region of the occlusion prior to an acute occlusion event. This pressure, in turn, may be utilized as a target pressure for the blood or other oxygenated medium which is being perfused distal to the occlusion. That is, it may be desirable to treat the measured "background" pressure as a maximum desirable pressure for perfusion in order to prevent injury to the vasculature distal to the occlusion.

Figure 7:
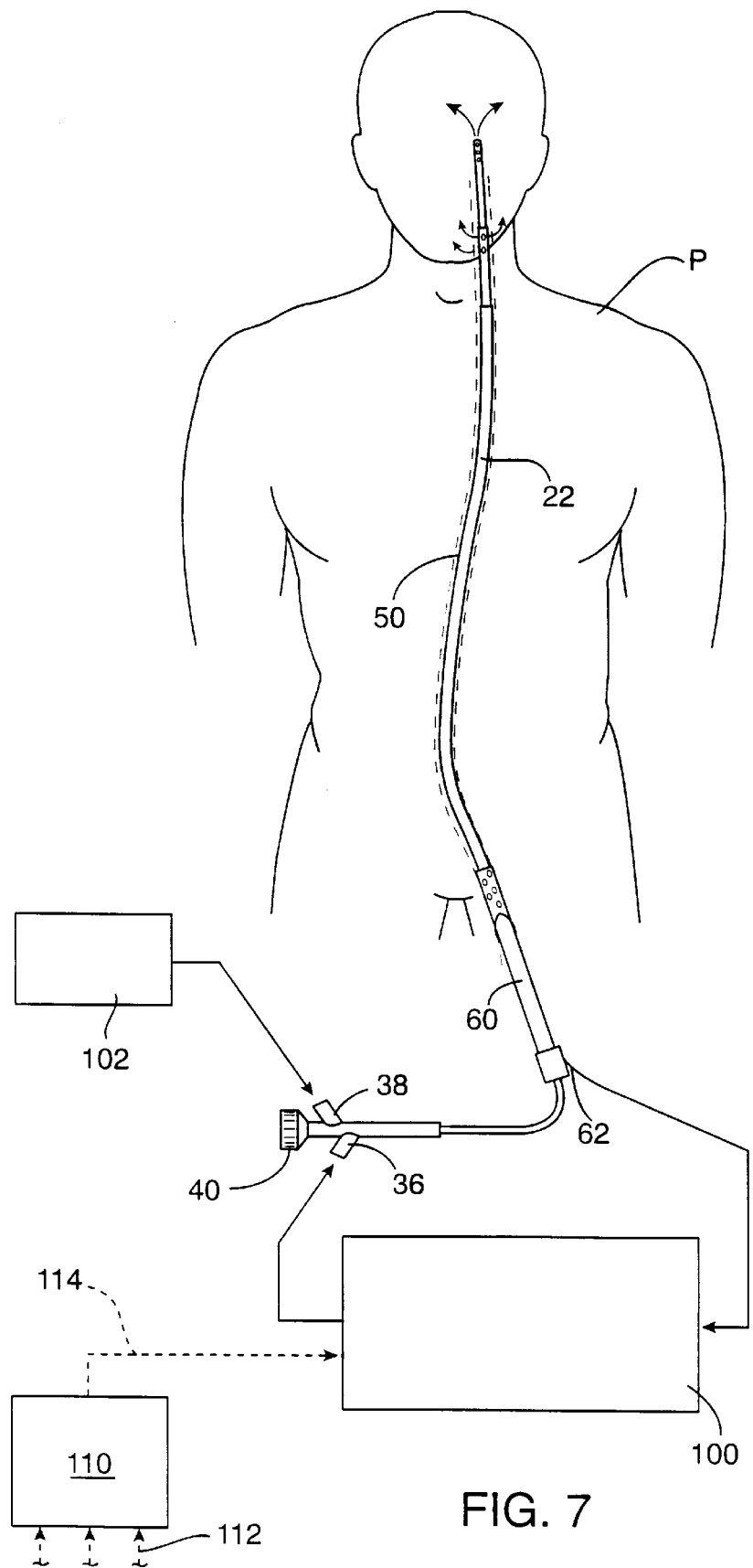
FIG. 7 illustrates a protocol using the system of FIG. 2 for treating a cerebral occlusion according to the present invention.
Figure 8:
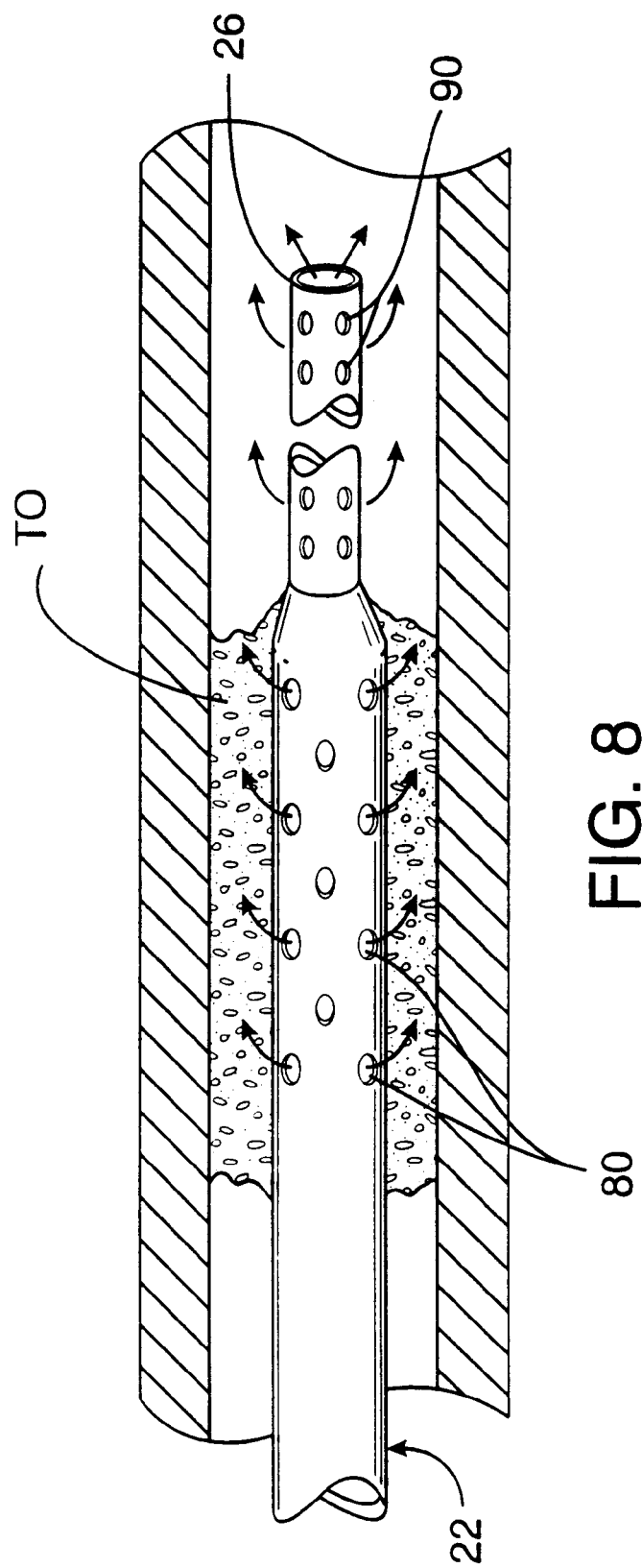
FIG. 8 is a detailed view of the catheter used for treating the occlusion in the protocol of FIG. 7.

Referring now to FIG. 7, use of the system 20 for treating the cerebral vasculature of a patient P will be described. Access to the target cerebral artery is established using the sheath 60 in a conventional manner. The guiding catheter 50 is then introduced through the sheath 60 and establishes a protected access lumen to a location within the cerebral vasculature. The catheter 22 is then introduced through the guiding catheter to the target site within the cerebral vasculature, typically over a guidewire (not illustrated). Conveniently, the catheters will be partly radiopaque and/or radiopaque markers 92 (FIG. 2) will be provided at the distal tip of the catheter as well as on either side of the drug ports 80 so that the catheter 22 may be properly positioned under fluoroscopic guidance relative to the obstruction being treated. After the tip 26 of the catheter 22 is penetrated through the occlusion TO (FIG. 8) the penetrations 80 are preferably located within the occlusive material in order to deliver the thrombolytic or other agent to the material. The distal portion of the catheter, including ports 90, in contrast, are located beyond the occlusive material in order to provide the desired blood perfusion. Blood flow is immediately established using an external pump 100 which receives blood from the port 62 of access sheath 60 and returns the oxygenated blood to the catheter 22 through port 36. A therapeutic agent, typically a thrombolytic agent, may be simultaneously introduced through port 38 from a source 102 in order to treat the occlusion TO. Optionally, the blood may be cooled before, during, or after it has passed through the pump unit 100. Still further optionally, the blood may be oxygenated or superoxygenated using an oxygen-saturated bubble chamber or conventional cardiopulmonary bypass oxygenators. In some instances, it may be desirable to combine the thrombolytic agent with a portion of the recirculating blood before infusing the thrombolytic agent/blood back through the port 38.

Figure 9:
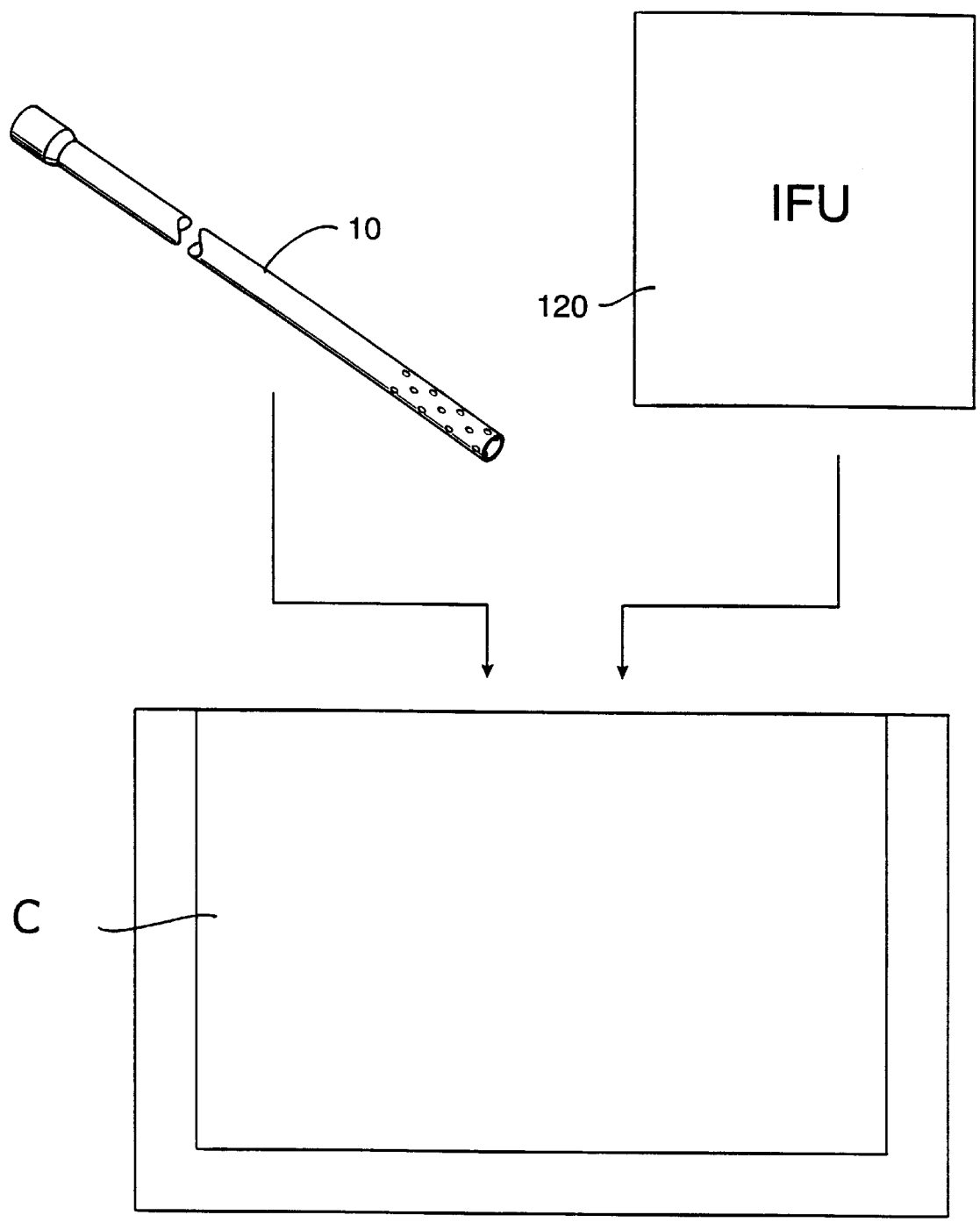
FIG. 9 illustrates a kit including components according to the present invention.

Kits according to the present invention are illustrated in FIG. 9. The kit will include a perfusion conduit, such as perfusion conduit 10, as well as instructions for use 120. The catheter and instructions for use will usually be combined within a suitable container C, such as a pouch, tray, box, tube, or the like. The catheter and possibly other components of the system (such as guide catheters, sheaths, thrombolytic or other therapeutic agents, disposable cartridges for pump/oxygenation systems, or the like) will optionally be included and/or sterilized within the packaging. The instructions for use may be on a separate sheet of paper or may be printed in whole or in part on the packaging materials.

Figure 10:
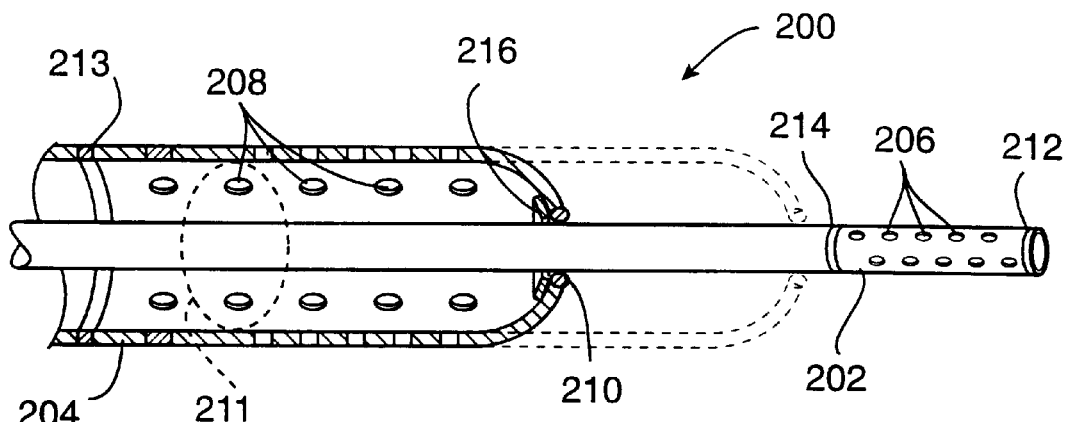
FIG. 10 illustrates an alternative embodiment of a perfusion conduit constructed in accordance with the principles of the present invention.

Referring now to FIG. 10, a perfusion conduit 200 includes an inner tube 202 and outer tube 204. The inner tube has perfusion ports 206 formed in its side wall over a portion of the distal end, and the outer tube 204 has perfusion ports 208 formed over a portion of its distal end.

The perfusion conduit 200 differs from catheter 22 primarily in that the inner tubular member 202 is able to slide axially relative to the outer tubular member 204. A sliding seal 210, typically an O-ring or similar passive seal, is provided to maintain pressure within the lumen of outer tubular member 204 so that thrombolytic and other drugs can be delivered without excessive loss through the distal tip. Some loss of the agent, however, will usually be acceptable so that the seal need not be completely tight. If a more positive seal is desired, an inflatable balloon 211 (shown in broken line) may be provided in addition to or in place of the sliding seal 210. Use of the balloon 211 is advantageous in that it permits higher infusion pressures without leakage from the distal end of the outer tube 204, but disadvantageous in that it limits the range of axial placement of the outer tube 204 relative to the inner tube 202. Use of the inner tube 202 for perfusing blood or other oxygenated medium therethrough will generally be as described with the prior embodiments. Radiopaque markers 212 and 214 on the inner tube 202 will be positioned distally of the occlusion to assure that the perfusion ports 206 will release the delivered blood with minimal resistance. Radiopaque markers 216 and 218 on outer tube 208, in contrast, will be positioned so that the infusion ports 208 lie generally within the occluded region. Optionally, the balloon 212 will be inflated to both lock the inner and outer tubes relative to each other and to provide a positive seal at the distal end of the outer tube, and the thrombolytic or other therapeutic agent will then be delivered through the lumen of the outer tube into the occlusive material, such as thrombus.

Figure 11:
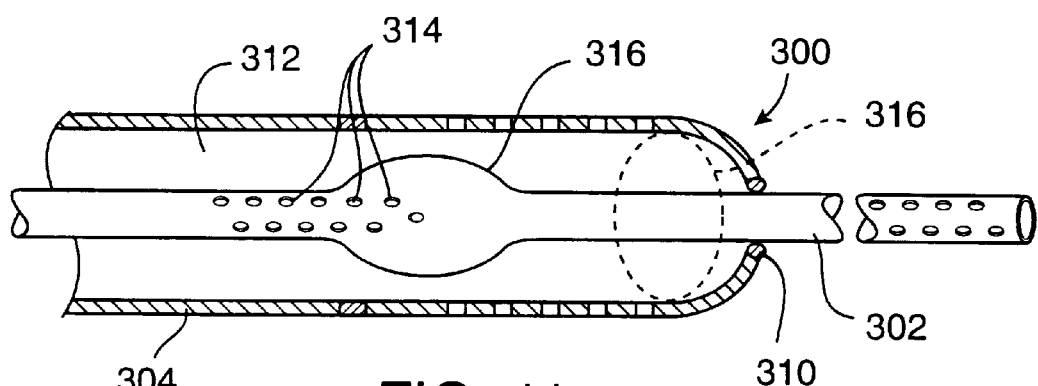
FIG. 11 illustrates yet a further embodiment of a perfusion conduit constructed in accordance with the principles of the present invention.

Referring now to FIG. 11, a perfusion conduit 300 also includes an inner tube 302 and an outer tube 304. The inner and outer tubes are slidable relative to each other, and a sliding seal 310 is provided at the distal end of the outer tube 304. The perfusion conduit 300, in contrast to prior embodiments, is not intended to deliver a therapeutic agent. Instead, it is intended only to perfuse blood or other oxygenated medium therethrough. The lumen 312 within the outer tube 304 is intended for passing the blood or other oxygenated medium to near the distal end of the conduit 300. The inner tube 302 then receives the blood or other oxygenated medium through ports 314 which permit the medium to flow from lumen 312 into the interior lumen of the tube 302. An enlarged portion 316 of the tube 302 is provided in order to prevent axial advancement of the tube so that the ports 314 cannot extend outside of the outer tube 304. Alternatively or additionally, an inflatable balloon 316 may be provided in order to both prevent excess axial advancement of the inner tube 302 and provide a more positive seal. Usually, since the blood will be perfused at lower pressures than might be used for drug delivery, use of the balloon 316 for isolation will often not be necessary. The perfusion conduit 300 can thus provided reduced flow resistance for the blood or other oxygenated medium being returned to the patient through the conduit. Additionally, the ability to slide the outer tube 304 relative to the inner tube 302 helps the tubes be properly positioned relative to each other depending on the circumstances of the patient being treated.

Figure 12:
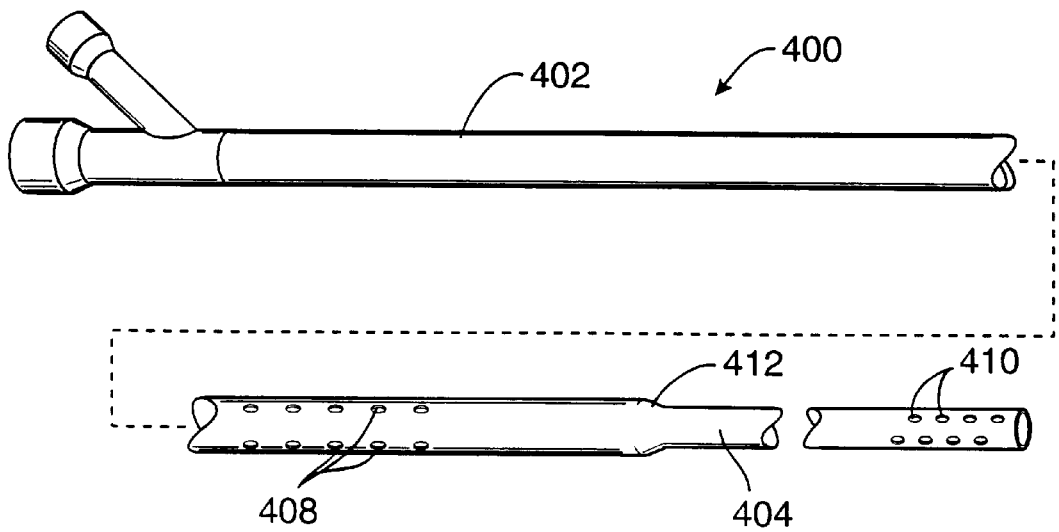
FIG. 12 illustrates yet another exemplary embodiment of a perfusion conduit constructed in accordance with the principles of the present invention.

Referring now to FIG. 12, a perfusion conduit 400 intended for passive perfusion, i.e., without active pumping, is illustrated. The catheter 400 usually comprises a single extrusion having a proximal section 402 with an enlarged diameter 412 and a distal section 404 with a reduced diameter. The proximal and distal diameters will generally be in the ranges set forth above. Blood inlet ports 408 are provided on the catheter near its proximal end while blood outflow ports 410 are provided near the distal end. The relative positions of the inflow ports 408 and outflow ports 410 allow the perfusion conduit 400 to be introduced to a patient so that the inflow ports are proximal to the occlusion while the outflow ports 410 are distal to the occlusion. The inflow ports 408 are usually relatively near to the distal end of the proximal section 402 having the enlarged diameter in order to decrease the overall flow resistance between the inflow ports 408 and outflow ports 410. Generally, however, the inflow ports 408 will be positioned so that they will lie proximally of the occlusion so that the occluding material does not block blood flow into the inflow ports. In some instances, they will be spaced proximally of the transition 412 from large diameter to small diameter by a distance in the range from 1 cm to 15 cm, usually from 2 cm to 10 cm, to assure proper placement in the vasculature. The inflow ports 408 are thus able to receive blood and pass the blood distally through the large diameter section with minimum pressure drop. A pressure drop through the narrow diameter section 404 will be greater, in many instances the total pressure drop of the conduit 400 will be sufficiently low so that adequate blood perfusion can be maintained to relieve patient ischemia. Optionally, the conduit 400 could have a slidable structure, as shown in conduit 300 of FIG. 11, but such structure will increase the flow resistance and will not be preferred in all instances.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating a patient having ischemia resulting from a pre-existing blockage in a blood vessel, said method comprising:
   penetrating a perfusion conduit through the blockage, wherein the perfusion conduit is free from external balloons; and
   pumping an oxygenated medium through the conduit at a rate or pressure sufficient to relieve ischemia but below that which would cause injury distal to the occlusion.

2. A method as in claim 1, further comprising oxygenating the medium prior to the pumping step.

3. A method as in claim 1, further comprising cooling the medium prior to the perfusing step.

4. A method as in claim 1, wherein the oxygenated medium is blood obtained from the patient.

5. A method as in claim 4, wherein the perfusing step comprises drawing blood from the patient and pumping the blood through the conduit.

6. A method as in claim 5, wherein the blood is drawn from a sheath percutaneously deployed with the perfusion conduit.

7. A method as in claim 1, further comprising delivering a therapeutic agent to the blockage and distally of the blockage or to the blockage only while pumping the oxygenated medium through the conduit.

8. A method as in claim 7, wherein the perfusion and therapeutic agent delivery steps are performed for a time sufficient to substantially reduce the blockage.

9. A method as in claim 8, wherein the perfusion and therapeutic agent delivery steps are performed for at least thirty minutes.

10. A method as in claim 9, wherein the perfusion and therapeutic agent delivery steps are performed for at least one week.

11. A method as in claim 1, wherein the blood vessel is in the cerebral vasculature.

12. A method as in claim 1, wherein the blood vessel is in the coronary vasculature.

13. A method as in claim 1, wherein the blood vessel is in the peripheral vasculature.

14. A method as in claim 1, wherein the blood vessel is in the mesenteric vasculature.

15. A method as in claim 1, further comprising monitoring pressure at a location where the oxygenated medium is being pumped back into the blood vessel.

16. A method as in claim 15, further comprising monitoring pressure at a location proximal to the blockage.

17. A method as in claim 15, further comprising controlling the rate or pressure of oxygenated medium being pumped in order to maintain pressure of the oxygenated fluid at the location where it is being pumped back into the blood vessel at a control point.

18. A method as in claim 17, wherein the control point is in the range from 50 mmHg to 300 mmHg.

19. A method as in claim 18, wherein the control point is increased over time from a value below the range to a value within the range.

20. A method for treating a patient having ischemia resulting from an occlusion in the cerebral vasculature, said method comprising:

percutaneously introducing a conduit into the patient's vasculature;

guiding a distal port on the conduit through the occlusion, wherein the conduit is free from external balloons;

obtaining oxygenated blood from the patient; and perfusing the blood back to the patient through the distal port of the conduit past the occlusion at a rate sufficient to relive the ischemia but below that which would cause injury distal to the occlusion.

21. A method as in claim 20, further comprising delivering a therapeutic agent to the patient while the pumping step is continued.

22. A method as in claim 21, wherein the therapeutic agent is delivered locally through the conduit.

23. A method as in claim 22, wherein oxygenated blood is perfused through a first lumen of the conduit and the therapeutic agent is delivered through a second lumen of the conduit.

24. A method as in claim 21, wherein the therapeutic agent is a thrombolytic agent, an anticoagulant, or an anti-restenotic agent delivered to the occlusion.

25. A method as in claim 20, wherein the percutaneously introducing step comprises introducing the conduit via the femoral, axillary, or brachial artery.

26. A method as in claim 20, wherein the occlusion is in an artery selected from the group consisting of the carotid artery, vertebral artery, proximal subclavian artery, brachiocephalic artery, and intracerebral arteries.

27. A method as in claim 20, wherein the obtaining step comprises withdrawing oxygenated blood from the same blood vessel into which the conduit has been introduced and the perfusing step comprises pumping the blood back through the conduit.

28. A method as in claim 27, wherein the oxygenated blood is withdrawn through a sheath introduced together with the conduit.

29. A method as in claim 28, wherein the sheath is disposed coaxially about the conduit.

30. A method as in claim 20, wherein the perfusing step comprises pumping the blood into the conduit at a rate in the range from 30 cc/min to 360 cc/min.

31. A method as in claim 30, further comprising monitoring blood pressure at a location where the blood enters the blood vessel.

32. A method as in claim 30, further comprising monitoring blood pressure at a location proximal to the occlusion.

33. A method as in claim 31, further comprising controlling the rate or pressure of blood being pumped in order to maintain pressure of the blood at the location where it enters back into the blood vessel at a control point.

34. A method as in claim 33, wherein the control point is in the range from 50 mmHg to 300 mmHg.

35. A method as in claim 34, wherein the control point is increased over time from a value below the range to a value within the range.

36. A method as in claim 20, wherein the obtaining and perfusing steps include drawing blood into proximal ports on the conduit and flowing the blood through the conduit in response to a natural pressure drop.

37. A method for treating a patient having ischemia resulting from an abrupt occlusion in the cerebral vasculature, said method comprising:

percutaneously introducing a perfusion conduit into the patient's vasculature within six hours of the occurrence of the abrupt occlusion;

guiding a distal port on the conduit through the occlusion;

obtaining oxygenated blood from the patient; and perfusing the blood back to the patient through the distal port of the conduit past the occlusion at a rate sufficient to relive the ischemia, wherein the pumping rate is controlled to maintain pressure downstream of the occlusion at a control point within the range from 50 mmHg to 300 mmHg.

38. A method as in claim 37, further comprising delivering a therapeutic agent to the patient while the pumping step is continued.

39. A method as in claim 38, wherein the therapeutic agent is delivered locally through the conduit.

40. A method as in claim 39, wherein oxygenated blood is perfused through a first lumen of the conduit and the therapeutic agent is delivered through a second lumen of the conduit.

41. A method as in claim 38, wherein the therapeutic agent is a thrombolytic agent, an anticoagulant, or an anti-restenotic agent delivered directly into the occlusion and/or distally of the occlusion.

42. A method as in claim 37, wherein the percutaneously introducing step comprises introducing the conduit via the femoral, axillary, or brachial artery.

43. A method as in claim 37, wherein the occlusion is in an artery selected from the group consisting of the carotid artery, vertebral artery, proximal subclavian artery, brachiocephalic artery, and intracerebral arteries.

44. A method as in claim 37, wherein the obtaining step comprises withdrawing oxygenated blood from the same blood vessel into which the conduit has been introduced and the perfusing step comprises pumping the blood back through the conduit.

45. A method as in claim 44, wherein the oxygenated blood is withdrawn through a sheath introduced together with the conduit.

46. A method as in claim 45, wherein the sheath is disposed coaxially about the conduit.

47. A method as in claim 37, wherein the control point is in the range from 50 mmHg to 150 mmHg.

48. A method as in claim 37, further comprising monitoring blood pressure at a location where the blood enters the blood vessel.

49. A method as in claim 37, further comprising monitoring blood pressure at a location proximal to the occlusion.

50. A method as in claim 37, wherein the control point is increased over time from a value below the range to a value within the range.

51. A method as in claim 37, wherein the blood is perfused for a period of at least 30 minutes.

52. A method as in claim 37, wherein the blood is perfused for a period of at least four hours.

53. A method as in claim 37, wherein the blood is perfused for a period of at least one week.

* * * * *